United States Patent
Sawafta

(10) Patent No.: US 7,146,384 B2
(45) Date of Patent: Dec. 5, 2006

(54) SYSTEM AND METHOD FOR DATA ANALYSIS, MANIPULATION, AND VISUALIZATION

(75) Inventor: Reyad I. Sawafta, Greensboro, NC (US)

(73) Assignee: TransTech Pharma, Inc., High Point, NC (US)

( * ) Notice: Subject to any disclaimer, the term of this patent is extended or adjusted under 35 U.S.C. 154(b) by 651 days.

(21) Appl. No.: 10/411,568

(22) Filed: Apr. 10, 2003

(65) Prior Publication Data

US 2004/0010515 A1  Jan. 15, 2004

Related U.S. Application Data

(60) Provisional application No. 60/371,956, filed on Apr. 11, 2002, provisional application No. 60/371,871, filed on Apr. 11, 2002, provisional application No. 60/371,644, filed on Apr. 10, 2002, provisional application No. 60/371,643, filed on Apr. 10, 2002.

(51) Int. Cl.
   G06F 7/00 (2006.01)
   G06F 17/30 (2006.01)
(52) U.S. Cl. .................. 707/104.1; 707/6
(58) Field of Classification Search ......... 707/4, 707/104.1, 6
   See application file for complete search history.

(56) References Cited

U.S. PATENT DOCUMENTS

| | | | |
|---|---|---|---|
| 5,550,964 A * | 8/1996 | Davoust | 345/440 |
| 5,914,715 A * | 6/1999 | Sasaki | 715/803 |
| 6,185,506 B1 | 2/2001 | Cramer et al. | |
| 6,207,861 B1 | 3/2001 | Nash et al. | |
| 6,356,256 B1 * | 3/2002 | Leftwich | 345/157 |
| 6,389,378 B1 | 5/2002 | Itai et al. | |
| 6,434,490 B1 | 8/2002 | Agrafiotis et al. | |
| 6,453,246 B1 | 9/2002 | Agrafiotis et al. | |
| 6,490,588 B1 | 12/2002 | Itai et al. | |
| 6,732,172 B1 * | 5/2004 | House et al. | 709/225 |
| 6,867,788 B1 * | 3/2005 | Takeda | 345/630 |
| 2002/0052882 A1 * | 5/2002 | Taylor | 707/104.1 |
| 2002/0095621 A1 * | 7/2002 | Lawton | 714/36 |
| 2002/0099506 A1 | 7/2002 | Floriano et al. | |
| 2003/0030637 A1 * | 2/2003 | Grinstein et al. | 345/420 |
| 2004/0172409 A1 * | 9/2004 | James | 707/104.1 |

FOREIGN PATENT DOCUMENTS

| | | |
|---|---|---|
| WO | WO 01/65349 A1 | 9/2001 |
| WO | WO 02/05209 A2 | 1/2002 |
| WO | WO 02/005209 A3 | 1/2002 |

OTHER PUBLICATIONS

Rick Mullin, "Accelrys Makes a Play for the Lab," www.cen-online.org, Mar. 17, 2003, pp. 17-18.

(Continued)

*Primary Examiner*—Don Wong
*Assistant Examiner*—Thanh-Ha Dang
(74) *Attorney, Agent, or Firm*—Kilpatrick Stockton LLP

(57) ABSTRACT

Systems and methods for data analysis, including data retrieval, dynamic scripting and execution, mining, storing, and visualization are dislcosed. One embodiment of this invention provides an integrated software solution for managing high volumes of numerical data quickly and efficiently. Another embodiment provides a complete and flexible solution for data acquisition, management, and manipulation. A further embodiment provides various views of assay data derived from a molecular discovery process.

15 Claims, 13 Drawing Sheets

OTHER PUBLICATIONS

Ermolaeva, O. et al., "Data management and Analysis for Gene Expression Arrays," Nature Genetics, New York, NY, US, vol. 20, Sep. 20, 1998 pp. 19-23.

Fellenberg, K. et al., "Microarray Data Warehouse Allowing for Inclusion of Experiment Annotations in Statistical Analysis," Bioinformatics (Oxford), vol. 18, No. 3, Mar. 2002, pp. 432-433.

PCT Search Report, Corresponding to PCT/US03/11180, mailed on Aug. 11, 2004.

Ermolaeva, O. et al., "Data Management and Analysis for Gene Expression Arrays," Nature Genetics, New York, NY, US, vol. 20, Sep. 20, 1998, pp. 19-23.

Fellenbgerg, K. et al., "Microarray Data Warehouse Allowing for Inclusion of Experiment Annotations in Statistical Analysis," Bioinformatics (Oxford), vol. 18, No. 3, Mar. 2002, pp. 432-433.

PCT Search Report corresponding to PCT/US03/11180 mailed on Nov. 8, 2004.

* cited by examiner

SYSTEM AND METHOD FOR DATA ANALYSIS, MANIPULATION, AND VISUALIZATION

CROSS-REFERENCE TO RELATED APPLICATIONS

This application claims priority under 35 USC 119 from U.S. provisional application Ser. No. 60/371,644, entitled "System and Method for Data Analysis, Manipulation and Visualization", filed Apr. 10, 2002; U.S. provisional application Ser. No. 60/371,956, entitled "System and Method for Data Analysis, Manipulation and Visualization", filed Apr. 11, 2002; U.S. provisional application Ser. No. 60/371,643, entitled "System and Method for Integrated Computer-Aided Molecular Discovery," filed Apr. 10, 2002; and U.S. provisional application Ser. No. 60/371,871, entitled "System and Method for Integrated Computer-Aided Molecular Discovery," filed Apr. 11, 2002. The disclosure of each of these provisional applications is hereby incorporated herein by reference. This application also relates to U.S. patent application Ser. No. 10/120,278 entitled "Probes, Systems, and Methods for Drug Discovery," filed Apr. 10, 2002 which is incorporated herein by reference. This application further relates to commonly assigned U.S. patent application Ser. No. 10/410,965entitled "System and Method for Integrated Computer-Aided Molecular Discovery", filed the same day as the present application. The disclosure of each of these U.S. patent applications is hereby incorporated herein by reference.

NOTICE OF COPYRIGHT PROTECTION

A portion of the disclosure of this patent document and its figures contain material subject to copyright protection. The copyright owner has no objection to the facsimile reproduction by anyone of the patent document or the patent disclosure, but otherwise reserves all copyrights whatsoever.

FIELD OF THE INVENTION

The present invention provides systems and methods for organizing, storing, retrieving, mining and otherwise using data. Embodiments of the present invention are advantageous for use with data generated through biological analyses.

BACKGROUND OF THE INVENTION

Large-scale analysis of numerical data can be an arduous task. Conventional systems provide user interfaces for analyzing data, however, they are extremely limited. In particular, conventional systems for setting up and performing tasks, such as molecular screening, are both inefficient and inflexible.

For example, in conventional systems for creating templates of plates used for screening compounds and probes, the design of the template is fixed. The user has no ability to make changes to the template based on the user's experience and technical expertise. In addition, once results are run, conventional systems are extremely limited in how generated data is displayed. For example, in conventional systems, changes to data may only be accomplished in a tabular view of the data, and the tabular and graphical views of the data may be incapable of displaying simultaneously. The user must constantly switch between the tabular view in which data is entered and the graphical view. Recalculation in such systems is entirely manual.

Another disadvantage with conventional systems is that to date conventional systems have been limited to single computing platforms. For example, a data analysis module may utilize Microsoft Excel for Windows. A system architecture that supports multiple computing platforms in a manner that is transparent to a user is not found in current systems.

SUMMARY OF THE INVENTION

The present invention provides systems and methods that overcome the limitations of heretofore utilized systems and provide numerous advantages.

Embodiments of systems of the present invention comprise a sophisticated architecture that supports multiple computer platforms, dynamic scripting, and parallel execution. The systems of the present invention advantageously allow the analysis, mining and management of large volumes of data in a fast, flexible and user friendly manner. Embodiments of the present invention are particularly well suited for use with the large volumes of biological data generated from high-throughput screening including: complex experimental protocols; flexible and dynamic assay layouts, multiple EC50 (Effective Concentration) and IC50 (Inhibition Concentration) determinations; interactive profiling and kinetic studies. Embodiments of the present invention allow access to and utilization of all available biological and chemical data from a screening protocol, across multiple computing platforms, in a highly integrated, flexible and fast manner.

Embodiments of this invention provide systems and methods for data analysis, including data retrieval, dynamic scripting and execution, mining, storing, and visualization. One embodiment of this invention provides an integrated software solution for managing high volumes of numerical data quickly and efficiently. Another embodiment provides a complete and flexible solution for data acquisition, management, and manipulation.

The types of data that a system according to this invention is capable of managing includes but is not limited to primary and secondary in vivo and vitro screening. An embodiment of this invention stores and integrates numerical data, such as biological and chemical data, in a database. The system uses an object-oriented approach for data analysis, programming, mining, storing, and visualization of the data.

Embodiments of this invention provide multiple advantages over conventional data analysis tools. A system according to this invention provides an integrated user interface in which to view and modify data. When changes are made to either tabular or graphical data, the user interface automatically changes the corresponding data in the other view(s). By automatically changing the data, the user avoids the problem of switching between views, which is common in conventional systems.

An embodiment of this invention also allows a user to manage diverse types of information, including, for example, information related to molecular discovery that ranges from large amounts of data generated from high-throughput screening programs, through multiple IC50 determinations and profiling, to complex experimental protocols and kinetics studies.

An embodiment of this invention also provides a highly flexible user interface. The user interface provides a layout feature. The layout feature of the system enables biologists to vary experiment parameters interactively. For example, using this feature, researchers can easily perform dose response titrations across several assay plates rather than having to create dose responses on single plates.

The user interface in an embodiment of this invention provides interactive curve-fitting capabilities combined with powerful graphic and charting tools for statistical analysis, a powerful query and reporting tool for creating structure-activity relationship reports, sample lists and profiles. To provide a richer and more intuitive user interface, each session's information is stored and easily retrieved through the 'DB Search' option, which is both fast and efficient.

An embodiment of this invention also allows the user to create customized templates for compound screening or other types of analysis. Controls, compounds, and concentrations can all be varied across a plate to allow for optimal placement. Due to this flexibility, an embodiment of this invention allows the user to make changes based on the user's expertise in the area.

An embodiment of this invention preserves the integrity of raw data. The application is fast and dynamic while maintaining the original data. The system can handle single or multiple plate analysis. Once the information is uploaded, it is stored in a centralized database. Any combination of templates can be defined; redefining controls as well as data locations as needed. The session is stored and readily available, for all future references. Thresholds are definable at a keystroke and can be adjusted for each experiment.

Further details and advantages of the present invention are set forth below.

BRIEF DESCRIPTION OF THE FIGURES

These and other features, aspects, and advantages of the present invention are better understood when the following Detailed Description is read with reference to the accompanying drawings, wherein.

DETAILED DESCRIPTION OF THE INVENTION

Figure 1:
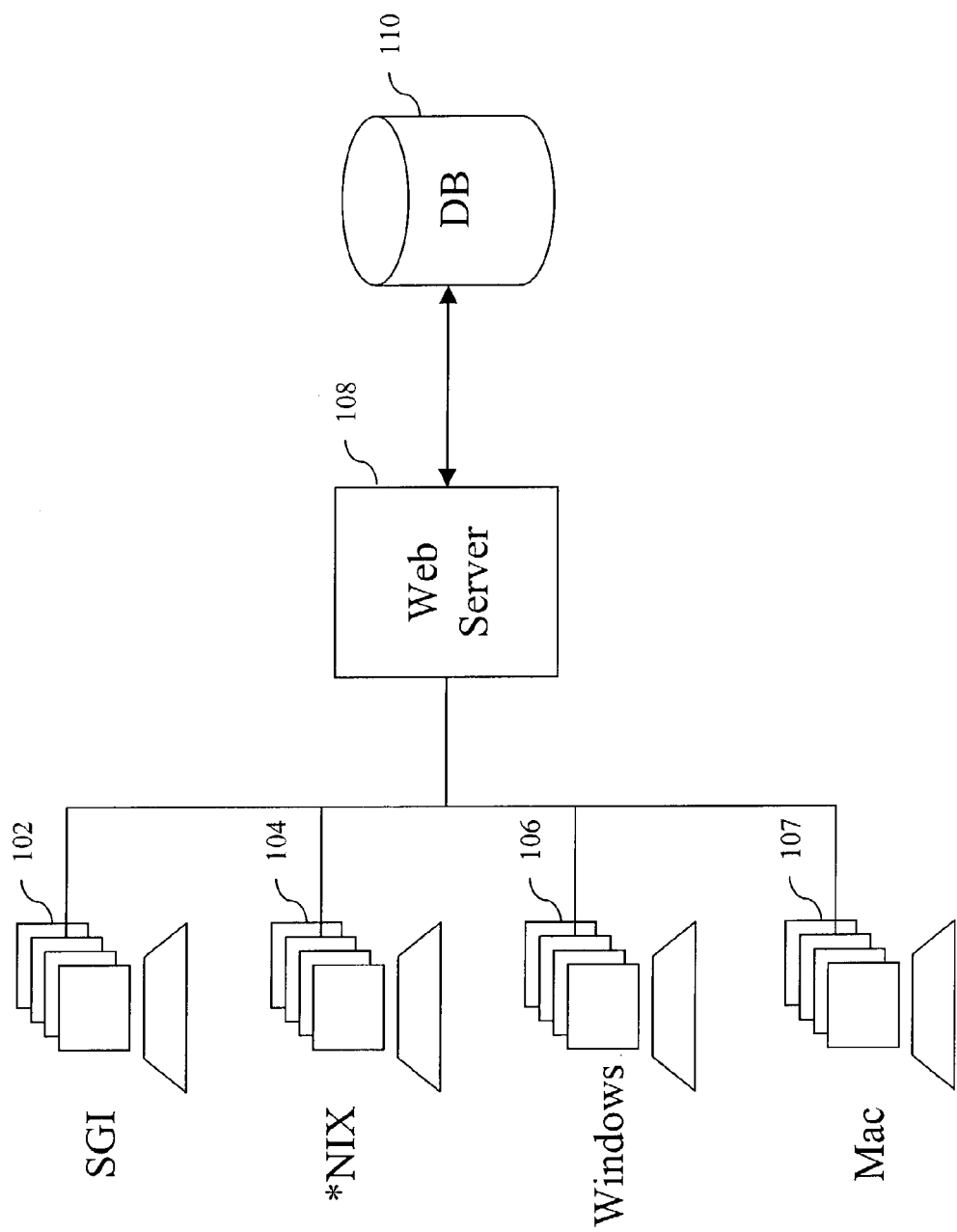
FIG. 1 illustrates an exemplary environment for an embodiment of this invention.

Embodiments of this invention provide systems and methods for data analysis, including data retrieval, dynamic scripting and execution, mining, storing, and visualization. One embodiment of this invention provides an integrated software solution for managing high volumes of numerical data quickly and efficiently. Another embodiment provides a complete and flexible solution for data acquisition, management, and manipulation. The types of data that a system according to this invention is capable of managing includes but is not limited to data relating to primary and secondary in vivo and vitro screening. An embodiment of this invention stores and integrates numerical data, such as biological and chemical data, from a database. A further embodiment of the present invention provides a display that allows visualization of multiple sets of graphical and/or alphanumeric data. The system may use an object-oriented approach for data analysis, programming, mining, storing, and visualization of the data.

In an embodiment, the present invention provides a data management system for managing data relating to a plurality of analyses, the system comprising: at least one data point for a first analysis; at least one data point for a second analysis; a first derived data point extracted from the data point for the first analysis; a second derived data point extracted from the second analysis; a display including each data point and each derived data point; a user interface permitting any of the data points to be excluded from the extraction of the derived data without changing the value of the excluded data point; wherein the display is capable of being dynamically updated to display updated derived data.

In embodiments, the system further comprises a first calculated data point calculated from the first derived data point and a second calculated data point calculated from the second derived data point. In these embodiments the excluded data point may comprise a derived data point or an initial data point.

In embodiments of the present invention, the data points, derived data points, and/or calculated data points may be displayed in a variety of manners including, but not limited to, display as tabular data; graphical data; alphanumeric data etc.

As described herein, embodiments of the present invention are particularly advantageous for use with data generated from the screening of biological entities. The data point from each analysis in the plurality of analyses may comprise the types of data conventionally generated in screening protocols, including but not limited to an entities structure; biological activity, including IC50 and EC50 data; analytical data; identification number and/or physical location. In high throughput screening, vast amounts of data are generated based on multiple analyses of an entity. In embodiments of the present invention, the data may be stored, mined, manipulated, displayed and otherwise analyzed.

In many embodiments of the present invention, sets of data from 10, 15, 25, 50, 100 individual analysis may be displayed and manipulated using the user interface.

Embodiments of systems of the present invention may operate in heterogeneous computing environment that includes multiple computer platforms with the same or different operating systems. For example, each computer may utilize at least one of UNIX, LINUX, WindowsOS, MacOS, and/or Solaris. The data extraction and user interface may be distributed among the computers in the heterogeneous environment. In an embodiment the system meets internet standards such that the system may be run in a heterogeneous environment as part of a corporate intranet, extranet, or similar network.

Embodiments of systems of the present invention provide flexibility to allow a user to determine a basis for excluding a data point from the extraction of derived data or the calculation of calculated data. The exclusion of a data point may be based, for example, on the relative value of the data point in comparison to a threshold level; and/or a data fit analysis. In embodiments the display will provide a visual indication of an excluded data point. For example the excluded data point may be highlighted, shown in a different color, italicized or treated in a similar fashion.

In embodiments the interface and display may comprise a graphical user interface. The graphical user interface may allow a user to point and click on data points to be excluded, for example using a mouse. The interface and display may also comprise a tool command line.

A further embodiment of the present invention provides an interactive data display system for viewing data relating to plurality of analyses comprising: alphanumeric data displays relating to at least a first analysis and a second analysis and graphical data displays relating to at least the first analysis and the second analysis; wherein the graphical data and the alphanumeric data are linked such that manipulation of the graphical data display will modify the corresponding alphanumeric data. Alternatively, or in addition, the system may further allow manipulation of the alphanumeric data display tp modify the corresponding graphical data. Embodiments of the present invention may be utilized for displaying alphanumeric data relating to additional analyses and displaying corresponding graphical data relating to the additional analyses. For example, alphanumeric data and graphical data for at least 10, 15, 25, 50, 100 or more analyses may be displayed.

The system may further comprise a data generation and analysis system for generating the alphanumeric data displays an/or a data generation and analysis system for generating the graphical data displays. The data generation and analysis system for generating the alphanumeric data displays may be the same or a different system than the data generation and analysis system for generating the graphical data displays.

A feature of the present invention is an interactive display system. In an embodiment an interactive display system for visualizing data comprises a display comprising a plurality of sections wherein each section includes at least a portion of the attributes of the display. The attributes of the display include, but are not limited to: images; objects; fields; labels; controls; hyperlinks; components; and/or options.

Another feature of embodiments of the present invention is a virtual assay plate system or virtual assay plate representation. This feature allows a user to define the composition of wells of an assay plate in real time without requiring the preparation of a template. The biological analyses referred to herein with reference to the present invention may advantageously be conducted using multiple well assay plates. The data relating to the composition of the wells, including for example, compound identification number, is utilized in systems of the present invention.

Further details relating to embodiments of the present invention are described below with reference to the appended figures.

FIG. 1 illustrates an exemplary embodiment of this invention. A user accesses the system via a users interface. In the embodiment shown, the user interface is a web-browser-based interface, which can execute on any number of platforms, including Silicon Graphics (SGI) 102, Unix and LINUX (*NIX) 104, Microsoft Windows 106, and the MacOS, 107.

A web server 108 generates the user interface. The web server 108 may utilize a variety of tools to generate the user interface, including common gateway interface (CGI), active server pages, (ASP), Java server pages (JSP), or other development tools. The web server 108 also receives parameters and requests from the user interface. For example, when the user fills out a form and submits the form to the web server, the web server receives the name-value pairs of the form fields as well as the next page to be processed. To generate the user interface and to respond to user requests, the web server 108 accesses a database (DB) 110, such as MySQL, Oracle, ISIS, and others. The web server 108 receives the request from the user, constructs a query, and submits the query to the database 110. The database 110 receives the query, executes the query, and passes the results back to the web server 108. The web server 108 receives the results, generates a new page based on or containing the results, and transmits the web page to one of the clients 102, 104, and 106 executing the user interface.

By utilizing a web-based approach, the embodiment shown in FIG. 1 is platform-independent, both in terms of the server and workstation. Any workstation capable of executing a browser, and any web server capable of supporting programming languages and features, such as C, C++, cookies, DHTML, Java, JavaScripts, PERL, servlets, Tool Command Language (TCL) and others, is capable of supporting the system.

An embodiment of this invention manages a wide variety of information in an integrated and flexible manner. For example, in one embodiment, a system according to this invention manages information related to molecular discovery. The data includes large amounts of data generated from high-throughput screening programs. The data may include, for example, multiple IC50 determinations and profiling of compounds, complex experimental protocols, and kinetics studies.

An embodiment of this invention provides a security layer to ensure that sensitive data is not compromised. An embodiment based on Internet standards uses common security methods, such as secured sockets layer (SSL) to implement security.

An embodiment also supports multiple users. For example, a web-based embodiment easily allows multiple sessions to be run simultaneously from anywhere within a network; the client simply utilizes a browser to execute the application. Processing of web server and database requests may be distributed within a heterogeneous cluster if necessary to support the load on the system.

An embodiment of this invention provides a highly flexible user interface. For example, in one embodiment, the user interface provides a assay plate layout feature. The layout feature provides a user with the capability of creating a virtual representation of an assay plate on screen. The layout feature of the system enables biologists to vary experiment parameters of the plate interactively. For example, using this feature, researchers can easily perform dose-response titrations across several assay plates rather than having to create dose responses on single plates. The researcher creates the representation of the plate by selecting compounds, concentrations, standards, controls, etc. and graphically "places" the compound into wells on the plate. Once the researcher is satisfied with the layout, he can save the plate layout and use it for multiple plates in the future.

The user interface in an embodiment of this invention may provide additional features as well. In one embodiment, the user interface provides interactive curve-fitting capabilities combined with powerful graphic and charting tools for statistical analysis, a powerful query and reporting tool for creating structure-activity relationship reports, sample lists, and profiles. In the embodiment, in order to provide a richer and more intuitive user interface, each session's information is stored and easily retrieved through a 'DB Search' option, which is both fast and efficient.

An embodiment of this invention may allow a user to process raw data from laboratory experiments. One embodiment of this invention preserves the integrity of the raw data. The application is fast and dynamic while maintaining the original data. The system can handle single or multiple plate analysis. Once the information is uploaded, it is stored in a centralized database. Any combination of templates can be defined; redefining controls as well as data locations as needed. The session is stored and readily available, for all future references. Thresholds are definable at a keystroke and can be adjusted for each experiment.

In one embodiment of this invention, the graphical user interface is highly customizable for each graphical and alphanumeric analysis. Where each set of data points is processed through a multi-threaded calculation and curve-fitting algorithm to display each plot quickly and efficiently. Using the GUI and keyboard routines, the user can make any number of changes to the plotter utility display, whether the changes can be the invalidation or revalidation of data points, resizing of the plotting areas, modification of the calculation formula, or any other feature available to the plotter utility, which dynamically updates the graphical and alphanumeric portions of the data such as curve fitting, plots and the statistical tables associated with them. The formula that is entered by the user to manipulate the data for curve fitting or statistical analysis can be flagged as either unique to a specific set of data or as globally affecting all the data sets being analyzed. Every configuration available for each plot1 such as X and Y lower and upper limits, displaying grid on or off, or other plotting specific features1 can also be flagged as unique to any particular set of data or as globally affecting all the data sets being analyzed.

In the embodiment shown, the plotter utility has the ability to section off areas of the plotting screen for a specific set of data. This feature allows for comparison between any combinations of other data sets all on one screen. The lotter utility can display any number of plots per page ranging from 1 to 100 or more, depending on screen resolution available and report preferences all using any combination of grid allocations and still manipulate them all, individually or any highlighted combinations. FIG. 2F illustrates 23 unique data sets being displayed in a 5-by-5 grid for easy comparison. Multiple pages are also available for the plotter utility to display a limited number of plots per page, in order to increase user readability and report presentations. The table displaying the relative data can also be updated when each page is displayed or flagged to display all the data values for comparison and reference.

When the user makes any changes to the plotter utility's data sets, such as invalidation or revalidation of data points or modification of the formula employed in curve-fitting or statistical evaluation, the original assay analysis data is also marked as invalid or revalidated according to changes made in other related data views, tables and displays. The formula used in the final plots is also saved for future retrieval of the data sets. The plotter utility directly accesses the database for it's plotting information and updates the modified data after each analysis. The plotter utility is an extremely powerful component of an embodiment because of its features and flexibility.

In one embodiment of this invention, the user interface is a graphical java-based application that is highly customizable for each analysis. Using the GUI and keyboard routines, the graphical component of the interface, the plotter utility, can be quickly suited for each user. The plotter utility directly accesses the database for plotting information and updates the modified data after each analysis. The plotter utility is an extremely powerful component of an embodiment because of its features and flexibility.

A system according to the present invention includes an easy to use analysis application that is dynamic, fast and efficient and can be used on any platform. An embodiment may includes many user-friendly features, such as custom templates, direct data access, centralized databases, flexible project creation and multi-plate projects. An embodiment may also include features that allow multiple users to simultaneously start new projects and return to previously completed projects. An embodiment is easily expandable for future experiment types and methods.

One embodiment of this invention allows the users to create dynamic reports at the click of a button. One report includes well shading, which allows a user to quickly and easily determine experimental results. It is also versatile for both color and black-and-white printing. To optimize viewing and printing, one embodiment includes web-based reports that are specially formatted for standard web page layouts.

Figure 2A:
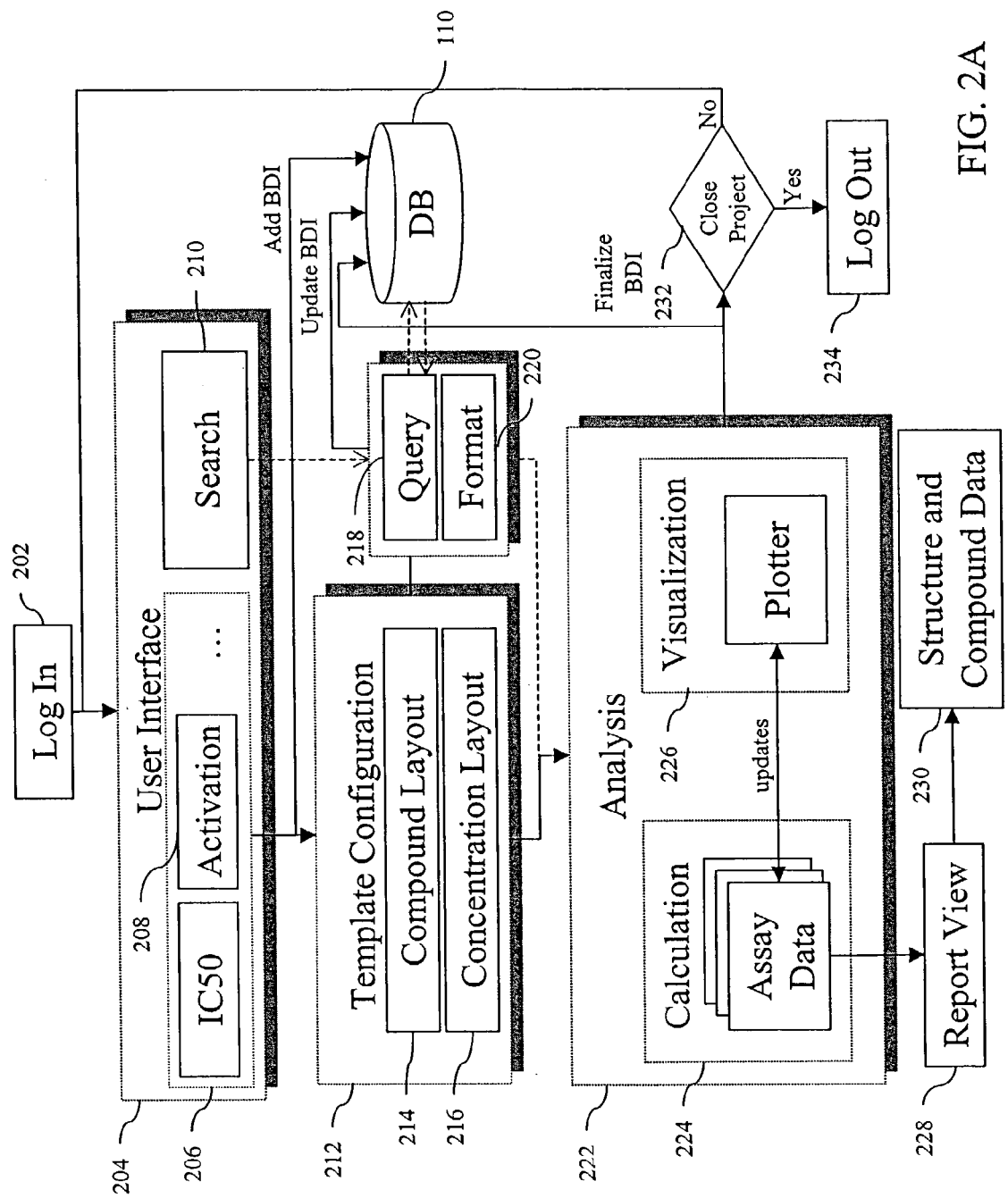
FIG. 2A illustrates a process in an embodiment of this invention.
Figure 2B:
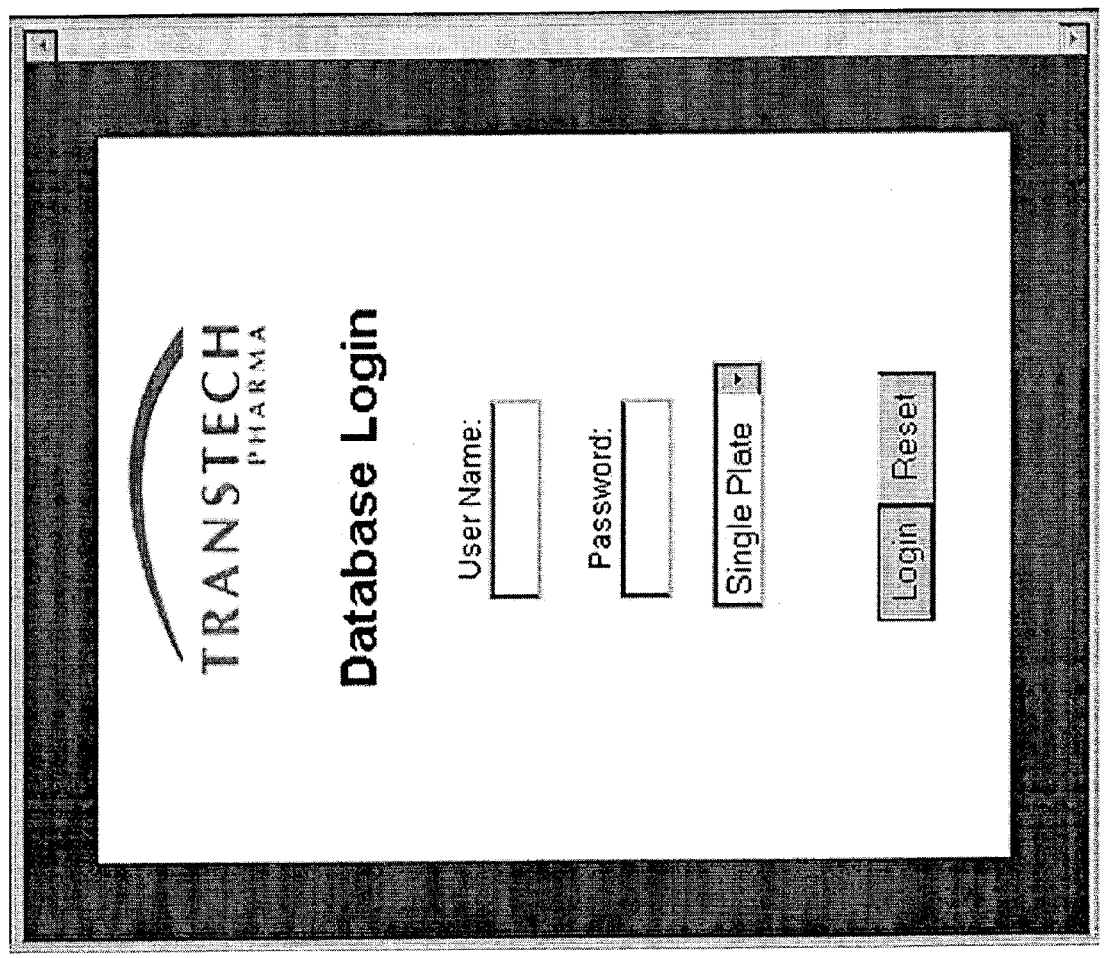
FIG. 2B is a screen shot of a logon screen in an embodiment of this invention.

FIG. 2A is a block diagram, illustrating the conceptual design of a scientific data analysis application according to this invention. FIGS. 2B–2F are screen shots of an embodiment implemented according to the logical design illustrated in FIG. 2A. In the description below, the various screen shots will be described with reference to the conceptual design.

In the embodiment shown, the user first logs in 202. Login may be accomplished in any number of ways. For example, in one embodiment, authentication is used so that the user is not required to type in a user name and password. In another user accesses a login screen and supplies a user name and password. FIG. 2B is a screen shot, illustrating such a login screen. In the login screen shown, the user supplies a user name, password, and the type of analysis to be performed. When the information has been entered, the user clicks the login button.

Referring again to FIG. 2A, the system provides the user with a user interface 204. In the embodiment shown, the user interface includes various modules, including an IC50 modules 206, an Activation module 208, and a Search module 210. Because of the flexibility of the modular user interface, many other modules may be included in the interface.

In the embodiment shown, the user selects either to view (Search) or create (IC50, Activation) a template configuration 212. The template configuration 212 refers to a virtual representation of a plate that will be used to perform an assay. The user specifies various parameters related to the plate. For example, in the embodiment shown, the template configuration 212 includes a compound layout module 214 and a compound concentration layout module 216 with corresponding user interface attributes. The user uses these modules to specify or view where a compound is to be placed on a plate and what the concentration of each of the plate wells will be.

Figure 2C:
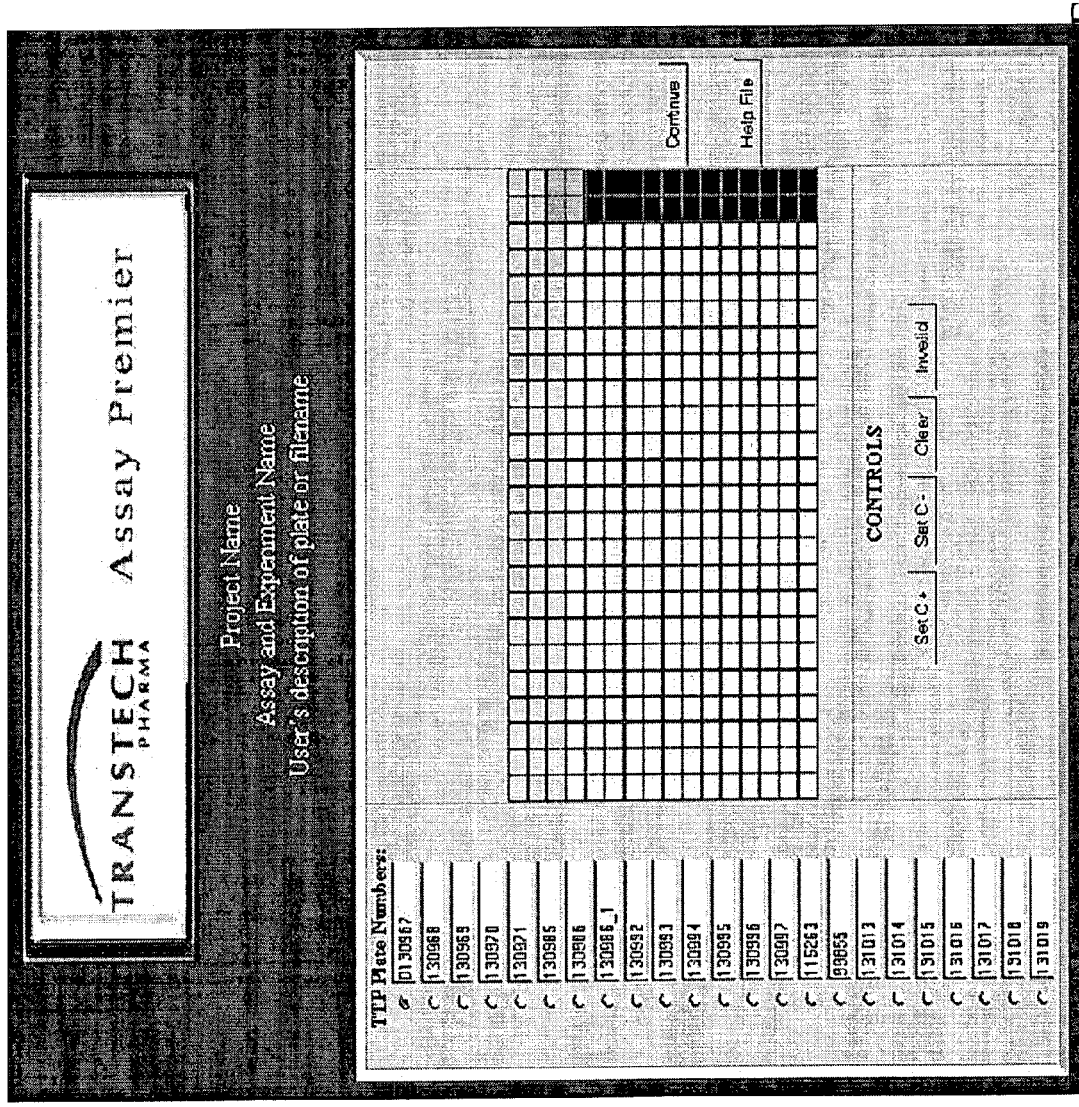
FIG. 2C is a screen shot of a template creation and modification screen in an embodiment of this invention.

FIG. 2C illustrates a compound layout screen in one embodiment of this invention. In the embodiment shown, multiple compounds can be "placed" on a plate. The user selects the compound from the list on the left. The user then clicks individual wells or clicks and drags across multiple wells, in any direction, or in any pattern, to specify where the compound is to be placed. In response to the users actions, the colors of the well change. When a compound on the left is selected, the wells in which the compound are to be placed are displayed in a contrasting color, for example blue. The user may also specify additional attributes of the plate, such as where the controls are to be placed, which wells are to be left empty, and others. When the user has completed the layout of the compounds, the user clicks continue. The layout is saved as a template configuration.

A user interface according to this invention may includes additional layout screens as well. For example, the embodiment shown in FIG. 2A also includes a concentration layout module 216. In one embodiment, the user accesses the concentration layout screen (not shown) immediately after the compound layout screen illustrated in FIG. 2C. In the concentration screen, the left column includes a list of concentrations that the user can add to, remove from, and select. As with the compound layout screen, the user selects wells to which to apply the concentration. When complete, each virtual representation of a well includes a compound attribute and a concentration attribute. As is clear to one skilled in the art, many other attributes of a well may be specified in this manner.

Figure 2D:
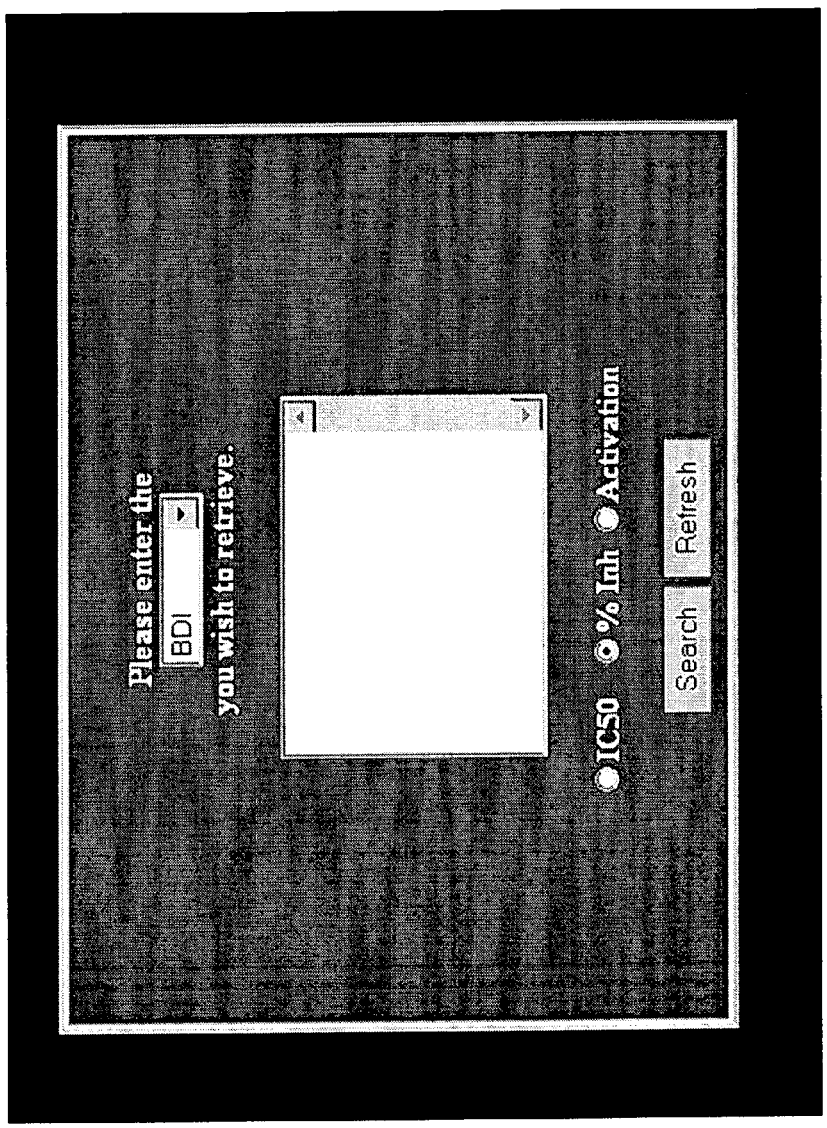
FIG. 2D is a screen shot of a search screen in an embodiment of this invention.

Referring again to FIG. 2A, the user my also perform a search. One embodiment of this invention utilizes a query component 218 to access a database (DB) 110. Results from the search are then formatted by a format component 220 and provided to some portion of the user interface 204, template configuration 212, or analysis components 222. FIG. 2D is a screen shot showing one embodiment of this invention that includes a form for searching for data. The user selects the search attributes and then clicks the search button.

Figure 2E:
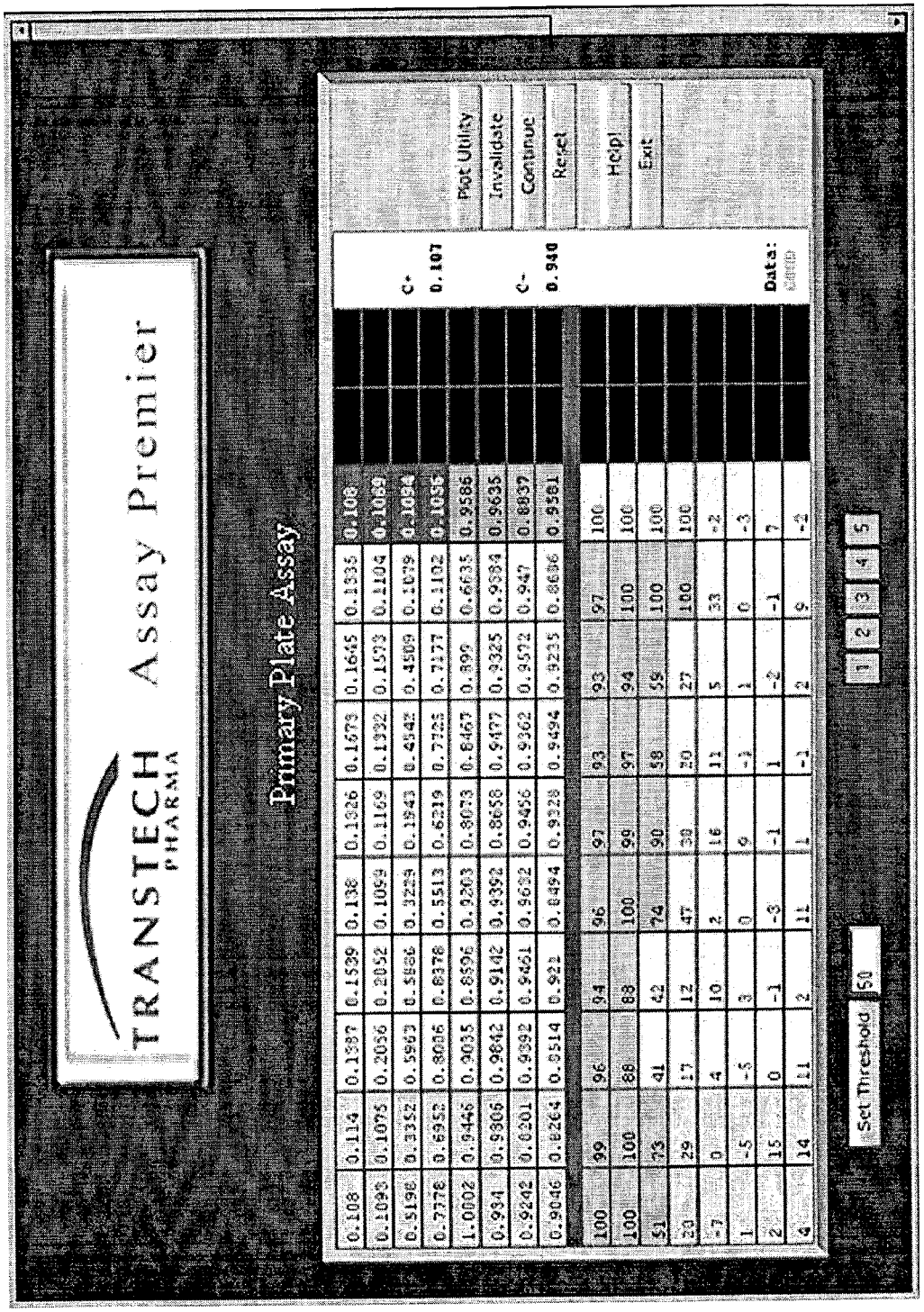
FIG. 2E is a screen shot of an assay data view in an embodiment of this invention.
Figure 2F:
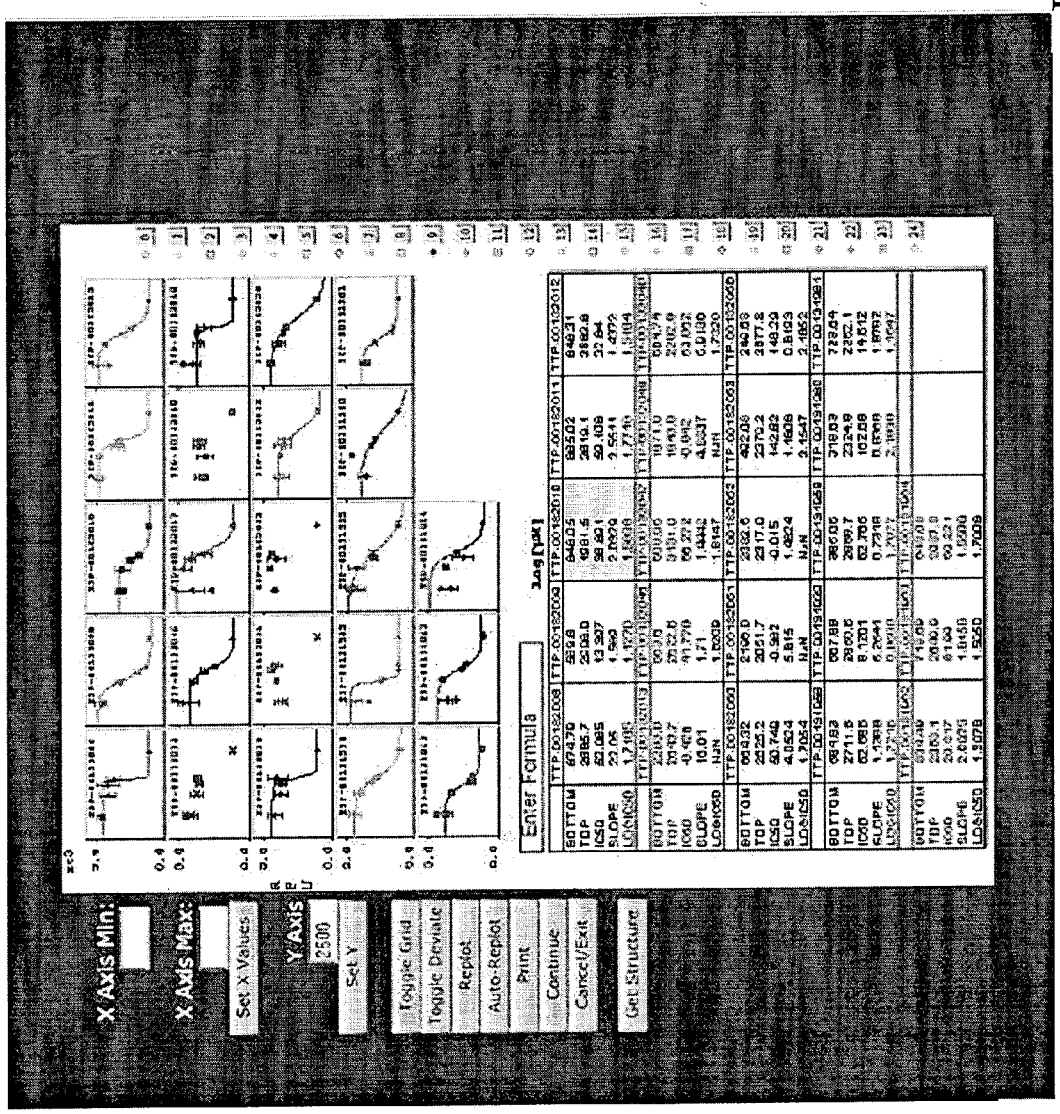
FIG. 2F is a screen shot of a plotter view in an embodiment of this invention.

When the user has completed the template configuration 212 or has retrieved and formatted 218 a previously existing template configuration, the embodiment shown provides an analysis module 222. The analysis module 222 includes an analysis interface. The analysis interface provides various views of the data including, for example, a calculation view 224 and a visualization view 226. FIGS. 2E and 2F are screen shots of a calculation view 224 and a visualization view 226, respectively. Importantly, in the embodiment shown, these views are not mutually exclusive. Also, data changes in one view are automatically and immediately made to the other corresponding view. Since it is critical in some applications that the integrity of raw data be maintained, one embodiment of this invention makes a copy of the raw data, and all changes to data occur on the copy of the data, leaving the raw data in its original state, neither altered nor deleted.

In the embodiment shown, assay data is displayed in the calculation or Assay Analysis view 224 shown in FIG. 2E and corresponding plots of the data are displayed in the visualization or plotter utility view 226 shown in FIG. 2F.

In an embodiment of this invention, the Assay Analysis view 224 may be implemented as a java or other modular component (herein referred to as techlet). The Assay Analysis techlet 224 combines the information gathered from the previous two views and information from a file that may be imported and parsed to display the raw data on the top half and the calculated values on the bottom half. An embodiment may utilize color-coding to enhance the usability of the techlet. For example, for a user to quickly identify which data set they are looking at, the currently selected compound is tinted blue. The user can change which compound they want to be selected by clicking on a numbered button in the user interface.

Additional features may be implemented to enhance the flexibility of the techlet as well. For example, from the Assay Analysis view 224, the user may highlight data points that are above preferred threshold by clicking and/or dragging over any number of wells. Highlighted wells are shaded with a dark-green and regular wells are shaded with a light-green. The user may also invalidate data points that are too extreme when compared to others in the same data set. Invalidated data will be displayed with a fine red X across the well. For applications in which the integrity of the raw data is necessary, invalidation of the data in the user interface does not affect the raw data; invalidation affects only the copy of the data.

When the user has completed analysis, manipulation, and visualization of the data, the user selects a control, such as a command button labeled 'Plot' to access the plotter utility view or techlet 226 and visibly interact with the data. An embodiment may include additional features as well. For example, a well that is invalidated within the Assay Analysis view 224 will be invalidated before the curve-fit and plot is calculated in the plotter utility 226. Also, any points that are invalidated during the plot configuration will also be invalidated on the Assay Analysis view 224.

As noted above, in an embodiment of this invention, the plotter utility 226 receives the data from Assay Analysis 224 and creates a plot, or multiple plots—one for each compound on the plate—and displays the first on the main window. To change between compounds to select and display, the user may click on any of the embedded java buttons to change selection or may press <1>~<0> for the first ten compounds, <Shift>+[<1>~<0>] for 11 through 20, and <Ctrl>+<Shift>+[<1>~<5>] for the remaining 21 through 25. Because of constraints on the size of a computer display, the maximum number of compounds displayed at any one time may need to be limited. For example, in one embodiment, the maximum number of compounds, which may be displayed at on time for plotter utility 226, is 25 compounds. If a user is analyzing more than 25 compounds, a user interface according to this invention may present the additional compounds on additional "pages" within the user interface while maintaining 25 or less compounds per page.

The processing requirements to update each of the plots in the interface may be high. One embodiment of this invention utilizes multiple threads to efficiently and quickly refresh the plots individually. In this manner, any changes that a user makes to a single plot require only the replotting of the individual plot and not a refresh of the entire displayed user interface.

In an embodiment, plotter utility 226 includes two views: a single plot and a mutiplot view. The single-plot allows for an enlarged and more detailed view of a single compound. If the user presses <ctrl>+[<2>~<5>] or <M>, then plotter utility 226 will change multi-plot mode and anywhere from a 2×2 to 5×5 grid and will display as many compounds as alloted space on the grid. Pressing <M> before any other grid size will display the maximum grid size of 5×5 by default; all future <M>s will toggle between last used grid-size and single-plot. Pressing <Ctrl>+<1> or <M> will return the display to the single-plot with the enlarged, detailed view of the currently selected compound.

The user may set the minimum and maximum ranges of the X and Y axis to best display their data by either entering limits on the HTML or by using the arrow keys to scale and shift the plot as needed. The values of the axis ticks and labels are dynamically recalculated and relabeled on each change. The <Shift> is used to accelerate the scaling and moving of the axis while the <Ctrl> is held or released to toggle between scaling and moving default is to scale. The named labels for On the currently selected compound, the user may invalidate any number of data points by clicking and dragging over them. When the user releases the mouse-button, the curve fit is recalculated and plotted if the curve succeeded in fitting to the data. If the curve is not able to fit the data points, then only the data points are displayed—no curve will be drawn. If a fit to the curve is made, but is unacceptable to the user, the user can press <Ctrl>+<Shift>+'click' on the compound either in the table or in the plotting region. When a compound is not plotted, the table changes all cell element values of the compound to dashes to indicate that the values are unacceptable.

The lower section of plotter utility 226 contains a table with each cell containing each compound. The elements of each cell refer to information displayed on the plot. On the single-plot view, if the user clicks on any cell, then that plot is now displayed in the main window and the cell is highlighted for quick reference. On the multi-plot view, if the newly selected compound is not displayed it will shuffle the currently displayed compounds in and out until the selected compound becomes visible and the table cell will highlight for the selected compound. If the newly selected compound is already displayed, only the table cell will highlight and nothing will be done with the main window.

When the user has completed their analysis of the plots created from their data points, the user may print the currently displayed plot(s) and clicks 'Done' to return to Assay Analysis 226 with their revised data now displayed on the plate layout.

An embodiment of this invention may include various keyboard controls to perform functions within the Assay Analysis 224 and plotter utility 226 views, both graphical and non-graphical, within the user interface. The following list of commands is utilized by one embodiment:

Keyboard Select:
1-0 Selects Compounds 1 through 10
Shift+1-0 Selects Compounds 10 though 20
Ctrl+Shft+1-5 Selects Compounds 21 though 25
Basic Keyboard Control:
'Left' Moves the data left
'Right' Moves the data right
'Up' Inceases the Y-axis Scale
'Down' Decreases the Y-axis Scale
Ctrl+'Left' Decrease the X-axis Scale
Ctrl+'Right' Increase the X-axis Scale
Shift+<dir >Multiple action by 5
'G' Toggles Grid View on or off
'D' Toggles Stadard Deviation Mode
'M' Toggles between Multi-Plot and Single Plot
Advanced Keyboard Control:
'A' Toggles Autoplotting on for dynamic plotting or off to speed up complex calculations
'R' Forces a replot of the data.
'I' Reinitialize plotter utility (soft restart of the application)
'[' Decrease overall Plot Screen
']' Increase overall Plot Screen
'O' Toggles Overlay Mode
'F' Toggles Formula Between Specific and Global
';' Cycle between pages
'P' Toggles plot settings between Specific and Global
'C' Toggles IC50 axis reference lines In other embodiments of the present invention, the user interface comprises interactive icons or buttons to perform the foregoing functions.

Additional views may also be provided in an embodiment of this invention. For example, the embodiment shown in FIG. 2A includes a report view 228. From thp report view, a user specifies a particular compound about which the user wishes to see additional details. The system then provides the user with a structure and compound data view 230, which provides details about the compound of interest.

In the embodiment shown in FIG. 2A, once the user is satisfied with changes to the copy of the data that the user is manipulating and viewing, the changes are saved to the DB 110. The user is asked whether or not to close the project currently displayed 232, and if the user responds affirmatively, the user is logged out 234.

Figure 3:
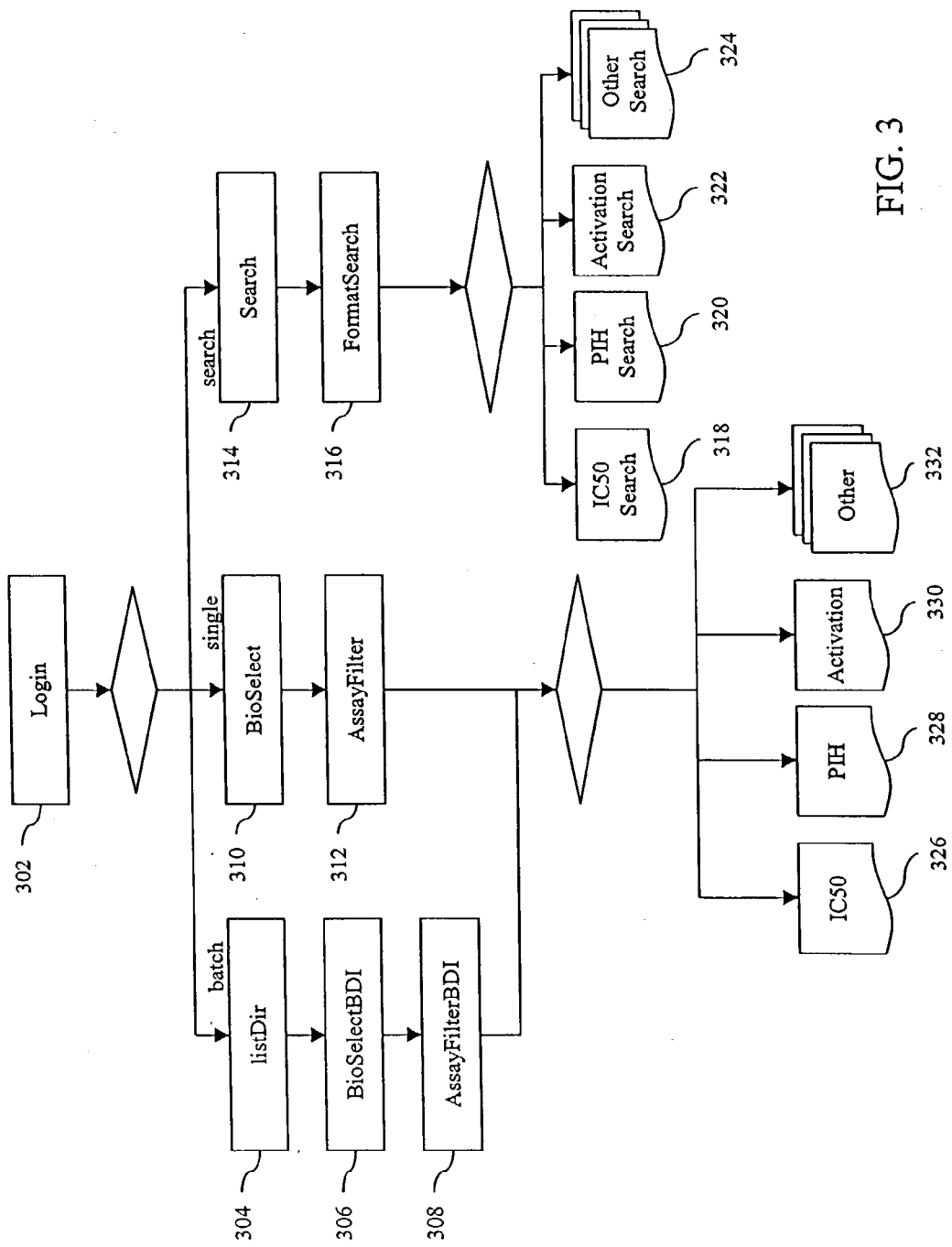
FIGS. 3–6 are process models of various embodiments of this invention.

FIG. 3 illustrates the process utilized by an embodiment of this invention in presenting the user interface and responding to user requests. In the embodiment shown, when the user accesses the system, the user must login 302. The system accepts username and password and allows selection of analysis or search options. Analysis includes Single or Batch analysis. In one embodiment as a web browser based application, the submit button on the page is clicked, and a cookie is set with the username and password. The application determines the next page to present based on the analysis type or search option selection.

If batch analysis is selected, they are directed to ListDir304. If the user selects single analysis they are directed to BioSelect 310. If 'Search' is selected, the user is directed to Search 314. In one embodiment, the next script is executed when the user clicks a command button labeled, 'Login'. The modules used to create the user interface, responds to user inputs, and perform program control may be one or a combination of any programming language, including but not limited to Perl, Java, C, C++, JavaScript, and web based user interface (e.g. HTML).

ListDir 304

In one embodiment of this invention, the ListDir component 304 uses a default network directory for file uploads. For a multiple plate analysis, the files to be used for this analysis are placed in a new folder within the default network directory. ListDir 304 reads the contents of the top default directory and lists them within the page with a checkbox next to each listing.

A 'Select All' command button causes all check boxes on the user interface page to be selected. 'Deselect All' causes all the checkboxes to be deselected. 'Invert Selection' reverses the checkbox selection. Clicking the command button labeled 'Submit' causes the program to call the BioSelectBDI module 306.

BioSelectBDI 306

In an embodiment of this invention, the BioSelectBDI component 306 provides the capability for a user to define the analysis session by target and experiment type for multiple files already uploaded into the user interface. Selection can be made between different calculation types and input parameters change according to the user's selection. In an embodiment implemented as a web-based user interface, HTML form elements are set dynamically as the user interacts with the page.

In one embodiment, a hyperlink is located at the top of the page that allows a user to redirect the project into a search mode. The hyperlink calls the script search.

A command button labeled 'Submit' causes a cookie to be set, which contains the selections. As described above, form elements are set based on user selections and the AssayFilterBDI component 308 is executed.

AssayFilterBDI 308

In one embodiment of this invention, the AssayFilterBDI 308 component uploads the files previously selected in ListDir 302, parses the files, and then inserts the data into the database. The user may be presented with additional options. Based on the selections made by the user or on a predefined logic flow in the BioSelectBDI component, the display component is executed. AssayFilterBDI 308 also determines the plate layout for the project.

To display a potable calculation type, the APTIC component (described below) is executed. If the calculation type is not potable, the appViewBDI component (described below) is executed next.

If any information is missing from previous submissions, the cookie is read. If the information needed is still not available, the system provides the user with a dynamically created submission display to supply the missing information, utilizing either the BioSelect 310 or BioSelectBDI 306 components.

Once the AssayFilterBDI component 308 is complete, output is created by an embodiment of this invention, including but not limited to IC50 326, PIH 328, Activation 330, and Other 332 output. Output may be displayed in the Assay Data 224 and plotter utility 226 views described above.

BioSelect 310

The BioSelect component 310 in an embodiment of this invention allows the user to define the analysis session by target and experiment type. The user uploads the experiment's data file into User interface. Selection can be made between different calculation types and input parameters change according to the user's selection. Form elements are set dynamically as the user interacts with the page.

The user interface may include a hyperlink on the page that allows a user to perform a search. The hyperlink calls the search component 314.

In one embodiment, when the user clicks a command button lageled 'Submit,' a cookie is set saving the selections, form elements are set based on user selections and form elements are submitted to the AssayFilter component 312.

AssayFilter 312

The AssayFilter component 312 uploads the file previously selected in the BioSelect component 310 to an archive directory and parses the data file, inserting the data into the database. Based on the selections made in the user interface under control of the BioSelect component 310, the next component is executed. The AssayFilter component 312 also determines the plate layout for the project.

In one embodiment, as with the AssayFilterBDI component 308, the AssayFilter component 312 executes the APTIC component (described below) to display a plottable calculation type. If the calculation type is not plottable, the AssayFilter component executes the dbParameters 404 component (described below in relation to FIG. 4).

If any information is missing from previous submissions, the cookie is read. If the information needed is still not available, the system provides the user with a dynamically created submission display to supply the missing information, utilizing either the BioSelect 310 or BioSelectBDI 306 components.

Once the AssayFilter component is complete, output is created by an embodiment of this invention, including but not limited to IC50 326, PIH 328, Activation 330, and Other 332 output.

Search 314

In an embodiment of this invention, to perform a search, the search component 314 first reads the username and password of the user from a cookie. The application next presents the user with a list of search parameters from which to choose, including but not limited to compound ID number, plate number or BDI number. The user enters the correct information for searching and selectes the type of calculation to be used for each item searched for. The calculation may be a predefined calculation, such as IC50, Activation, or Inhibition, or a custom calculation provided by the user. When a user clicks 'Search', the validity of input is checked, the cookie is updated and the form elements are submitted to the format_search component 316.

Format_Search 316

The Format_Search component 316 formats the search criteria on the basis of the search type entered by the user. For example, in one embodiment, if the user selects IC50 or Activation, the format_search component 316 calls the update DBIC50 component 410 (described below); otherwise the format_search component calls the appViewBDI2 component 512 (described below). Comparisons are made between the information in the database and the user defined selections. If an error occurs, or an improper selection has been made the component 316 detects the error and presents the user interface for Search to the user. If any information is missing, the cookie is checked for missing values. If the information is correct the page continues to the next script.

An embodiment of the present invention is capable of performing various types of searches, including but not limited to IC50 318, PIH 320, Activation 322, and Other 324 searches.

Figure 4:
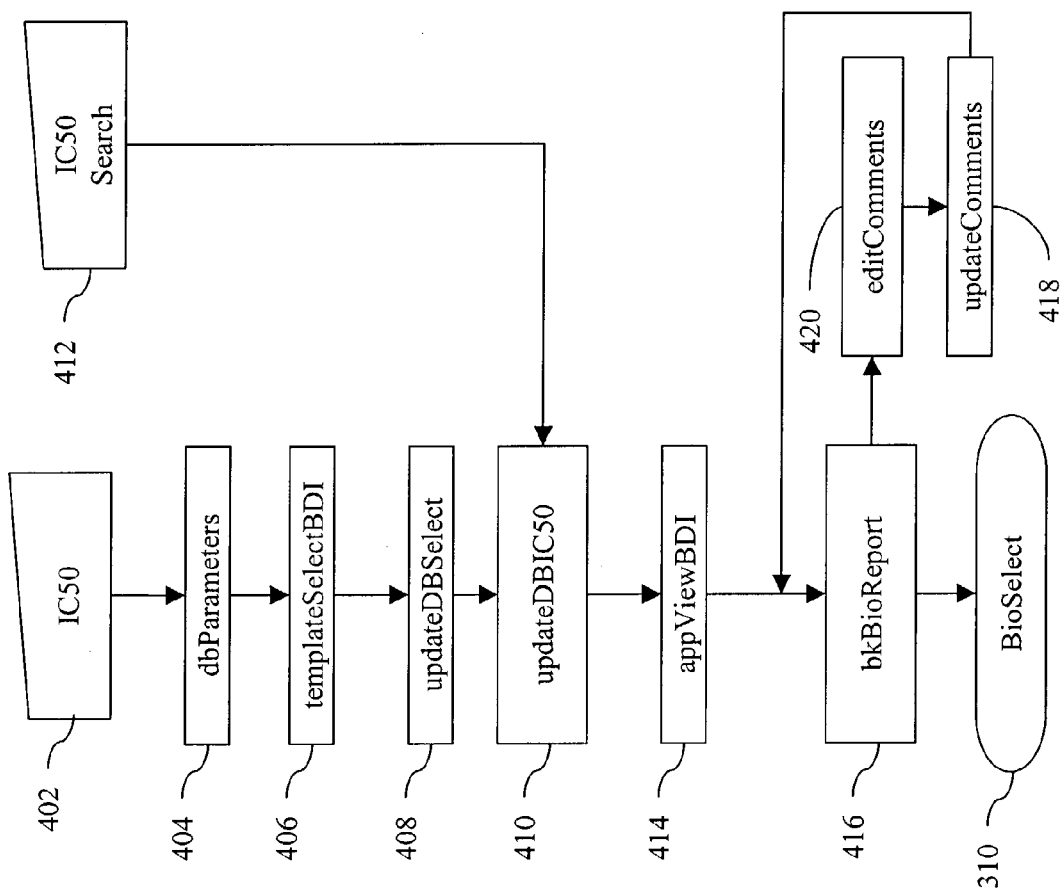
Figure 4A:
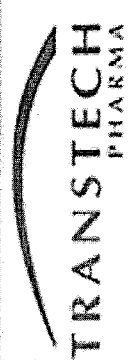
FIG. 4A is a screen shot of a search screen in an embodiment of this invention

FIG. 4 illustrates the process for analyzing and manipulating IC50 data in an embodiment of this invention. Many of the components utilized by an embodiment in performing an IC50 analysis, data manipulation, and search are also used for other types of searches. In such cases, the components are numbered similarly in FIGS. 5 and 6.

Dbparameters 404

In an embodiment of this invention, the dbparameters component 404 is a dynamic user interface, such as a web page, that is used to provide additional information useful for identifying submitted plates. In one embodiment, the interface includes controls in which a user enters numbers that identify the plate(s). These numbers are used to reference a corporate, proprietary, or other database structure for information relating to these plates.

In some instances, the layout of the plate is derived from previously submitted information within the database structure. In such a situation, the dbparameters component 404 uses this stored information to fill in at least some of the elements of the user interface, thereby limiting the demands on the user.

In one embodiment, if plate layout information is available, a template representing the plate is dynamically created from that information and displayed on the user interface within the project. The template may be modified by the user within the analysis portion of the user interface, alleviating the need for the user to move between user interface screens to make the modifications.

In an embodiment performing IC50 analysis, manipulation, and/or visualization, the dbparameters component 404 calls the templateSelectBDI component 406, passing the usersupplied or database-derived parameters. In other embodiments, such as for analyzing Activation and PIH, the updateBDI_Info component 506 is called.

templateSelectBDI 406

In an embodiment of this invention, the templateSelectBDI component 406 is a user interface component, such as a web page, that allows users to define a template for use in analysis. In a multiple plate analysis, this template is used for the batch of plates as well. This dynamic interface uses the information from the dbparameters component 404, either user or database-derived, and additional information from the database(s) to dynamically define a basic template.

Figure 4B:
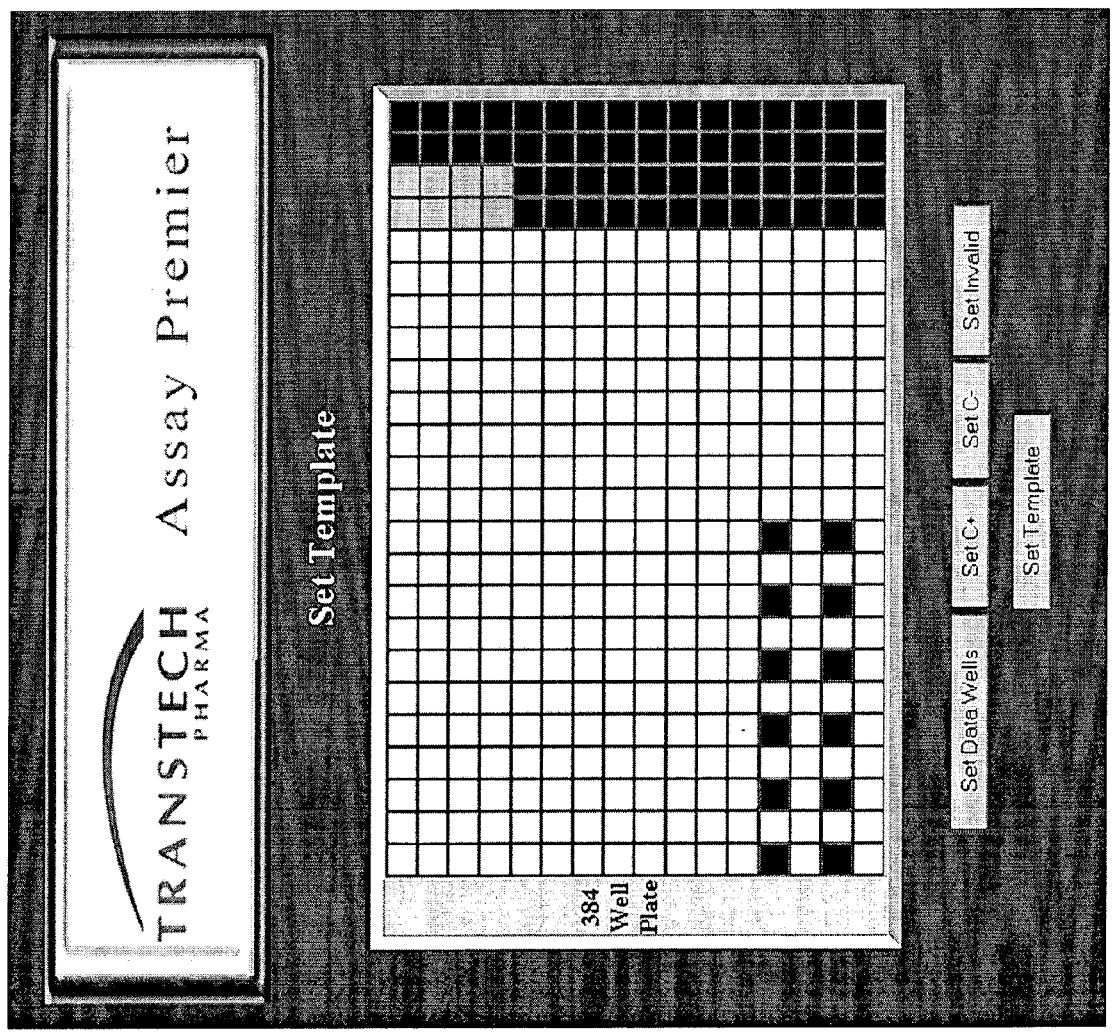
FIG. 4B is a screen shot of an assay plate set up in an embodiment of this invention.

In one embodiment, as illustrated by the screen shot of FIG. 4B, plate wells that do not contain compound are colored black. C+ and C− control wells are colored light-grey and dark grey, respectively. Compound wells are a default white.

The user interface provides a means to make changes to the templates. For example, in the embodiment shown in FIG. 4B, command buttons exist within the interface allowing the user to define the mouse interaction with the component or techlet. If the user clicks 'C+', mouse drags over the techlet will define C+ control wells. Likewise, if the user clicks 'C−', mouse drags over the techlet will define C− control wells. If the user clicks 'Invalid', the mouse defines empty wells, and if the user clicks 'Data' the mouse defines data wells.

Clicking 'Reset' in the embodiment shown, resets the techlet to the default calculated template. Clicking 'Submit' sets a cookie and page elements and submits the page elements to the updateDBselect component 410.

updateDBselect 410

In the embodiment shown, the updateDBselect component 410 receives data elements from the templateSelectBDI 408 component and updates the database with new values created via the template user interface. The component 410 then retrieves values from the database and calls the updateDBIC50 410 or appViewBDI 414 component.

updateDBIC50 410

In one embodiment, as shown in FIG. 4, the updateDBIC50 component 410 creates a connection to the database and retrieves the necessary data for the APTCO component (described below). The updateDBIC50 component 410 may also update the database with calculated values from an analysis session and may be executed several times within the session. It may use various other components to perform functions. For example, in one embodiment, the updateDBIC50 component calls the updateDBICflag, which updates the database with calculated values and any changes made relating to the analysis or compounds. In a further embodiment, the component 410 calls the APTCO component (described below).

appViewBDI 414

In one embodiment of this invention, the appViewBDI component 414 is a user interface generation script, such as a perl script that generates an html document. The user interface includes the Assay Analysis View component 224 described in relation to FIG. 2 above.

The user interface provides the user with a control, such as a text box, for specifying the screening threshold. Changes to the value are reflected in the view 224 either automatically or in response to a user action, such as clicking a command button.

In one embodiment, elements of the user interface are created dynamically. For example, in one embodiment, buttons are dynamically created for each compound. As each button is selected, the related compound is highlighted in the techlet 224. Clicking 'Continue' updates the cookie, sets form elements and calls both the bkBioReport 414 and updateDBcalc 516, updating the database and generating a printable report through the script bkBioReport. The button 'Help', displays help.

If multiple plates have been submitted for the current session, buttons appear at the bottom of the techlet 224, allowing navigation through the array of plates. The buttons indicate usage by arrows. The button first allows a user to go to the first plate. The next button allows navigation to the previous plate display. The third button navigates to the next page and the last button navigates to the last plate in the plate array.

updateBDI info 506

The updateBDI_info component 506 is a background component used for database updates. It accepts the information gathered by the dbparameters component 404 and updates the database. In one embodiment, if information is missing from dbparameters 404, the updateBDI_Info component recalls the dbparameters user interface. If successful, it calls the templateSelectBDI component 406.

updateDBcalc 516

Figure 5:
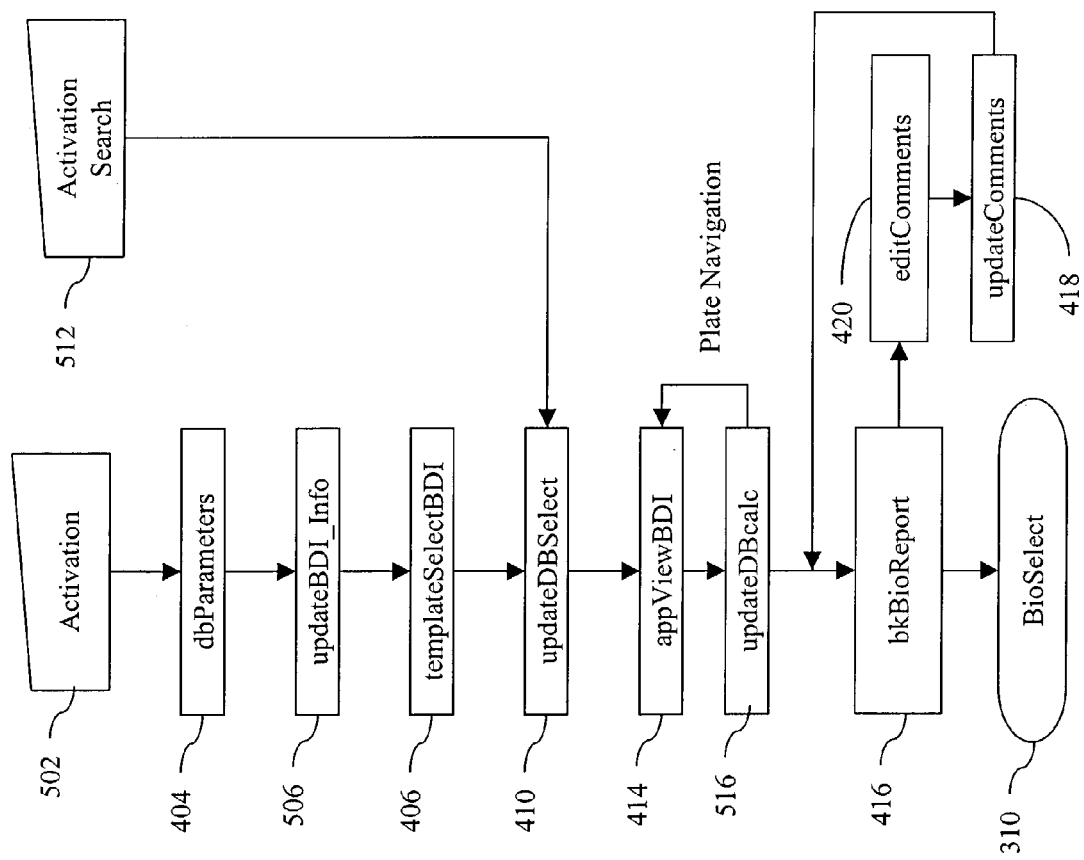
Figure 6:
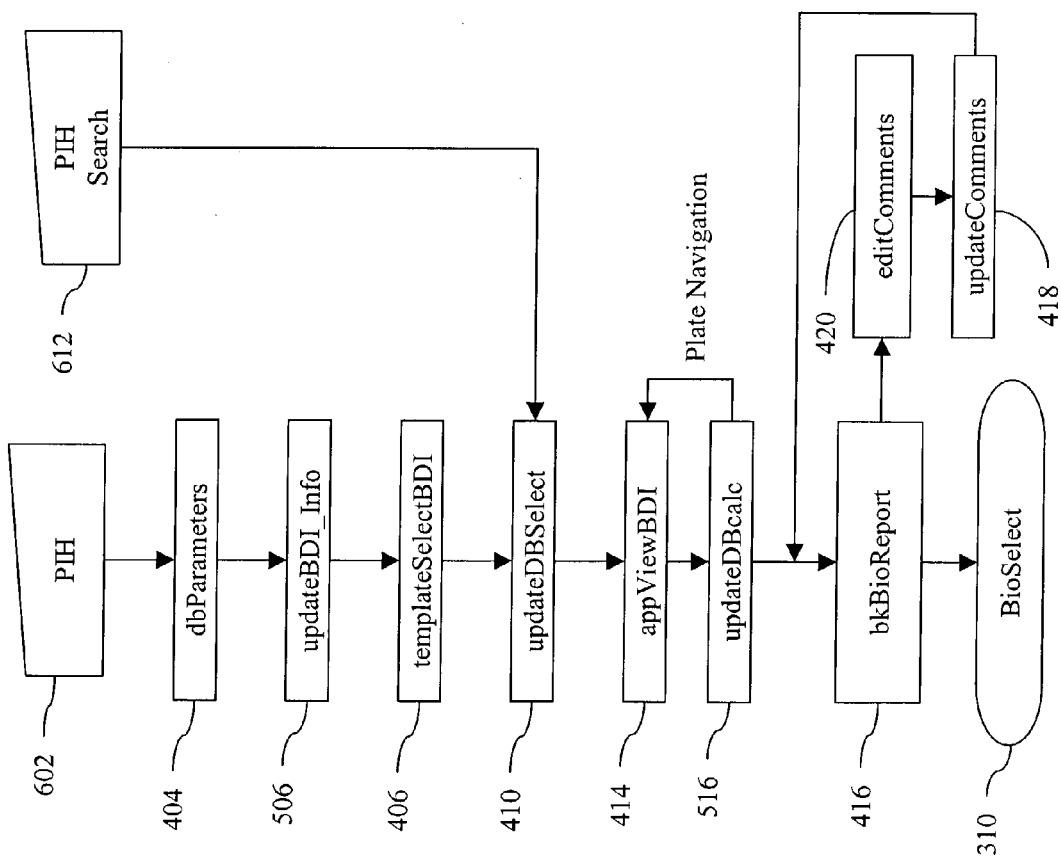

In the embodiments of this invention shown in FIGS. 5 and 6, the updateDBcalc component 516 accepts the updated form elements from appViewBDI 414 and updates the database. This component 516 to subsequent components based on user input; if 'Continue' is selected by a user, the component 516 calls the bkBioReport component 416. If the user is analyzing multiple plates and has selected 'Next', 'Previous', 'First', or 'Last', the appViewBDI component 414 is executed, passing the appropriate parameters to complete the user's request.

APTIC

The APTIC component (not shown) is a component that creates a user interface, such as an HTML page housing a techlet. The user interface allows the user to define the location of compounds within a plate layout. APTIC calls the APTIC2 component (described below).

APTIC2

The APTIC component (not shown) is a component that creates a user interface, such as an HTML page housing a techlet. The user interface allows the user to define the location of concentrations within a plate layout. APTIC calls the APTCO component (described below).

APTCO

The APTCO component creates a user interface that displays the relationships between compound and concentration definitions defined in the previous two components (APTIC and APTIC2). The techlet formulates calculated values dynamically based on the calculation type and the raw data from the data file. If any elements are not present from the database query done by updateDBIC50 410, they are retrieved from the cookie.

The user interface includes a Screening Threshold control as described above.

Additional user controls, such as buttons, are dynamically created for each compound. As each button is selected, the related compound is highlighted in the techlet. The compounds can be plotted by clicking the 'Plot' button. This calls updateDBIC50 410. By clicking 'Invalidate', wells within the plate layout can be removed from the calculation. Clicking 'Continue' updates the cookie*, sets form elements and calls both bkBioReport (described above) and updateDBICflag (described above in relation to the udpateDBIC50 component 410), updating the database and generating a printable report through the script bkBioReport2.

Plotter Utility

ICplotBDI (not shown) is executed by APTCO. In one embodiment, the component is a Perl script that generates a HTML document housing a techlet. This techlet dynamically plots the compounds. The techlet also incorporates keyboard and mouse interaction to change aspects of the plotting application.

Buttons are located on the page for interaction with the techlet as well. By entering values within appropriate text boxes and clicking 'Set Y Axis' or 'Set X Axis' the axis value within the techlet are changed. By clicking 'Grid', a visual grid toggles within the techlet display. Clicking 'Deviate' causes the display to show a deviated calculation display. For example, the average and standard deviation of a data point may be plotted instead of individual data points at the same concentration, i.e., an experiment may be run multiple times so that a user can show all data points or take an average and a standard deviation of these points.

In one embodiment, the button 'Replot' causes a manual recalculation of the plot(s). 'AutoPlot' is a button that, when clicked, toggles the techlet's plotting status. In the 'on' state, the techlet automatically replots after any change is detected however, in the 'off' state the techlet does not automatically redraw itself after a change and must be manually replotted using the 'Replot' button. 'Print', when clicked, prints the techlet. 'Get Structure' is another button that when clicked calls a script called QueryChem.

In one embodiment, when 'Continue' is clicked, updateDBIC50 and updateDBICflag are called. These two scripts update the database with the changes made within the techlet and APTCO is refreshed incorporating the changes made while plotting.

If the user clicks 'Close', the plotter is closed and no changes are recorded.

QueryChem

In an embodiment of this invention, QueryChem (not shown) is a component, such as a script, that generates a HTML form that automatically submits itself to infosearch.html on a separate server.

bkBioReport2

In one embodiment of this invention, the bkBioReport2 component (not shown) is a dynamic perl script that generates a printable report with three tables. The first is a table displaying raw data in a relative plate format. The second displays calculated percent inhibition values in a relative plate format. The third displays the percent inhibitions sorted by compound ID and concentration, including an average and standard deviation for each concentration per compound.

The tables are color-coded based on values defined in APTCO and the plotter utility. Green indicates compounds that showed inhibition based on the user defined threshold value. Red indicates an invalid point, not used in calculation. Light Grey indicates C+ and a darker grey indicates a C− value.

Located at the bottom of the page is a legend describing the color codes and three buttons. The first button is 'Print', which prints the report. The second button is executed 'Return to Upload'. When clicked, 'Return to Upload' causes the current project to close and returns the user to BioSelect. The third button is executed 'Edit Comments'.

When 'Edit Comments' is clicked, a script called editComments is executed that allows a user to edit the comments stored in the database relating to the analysis session.

bkBioReport 416

In an embodiment of this invention, the blkBioReport component 416 generates a printable report containing data tables. For example, in one embodiment, the component 416 creates three tables. The first is a table displaying raw data in a relative plate format. The second displays calculated percent inhibition values in a relative plate format. The third displays the compounds that showed inhibition based on the user-defined threshold in a list format, sorted by inhibition value. The list identifies the compound by ID as well as plate and well location. The compound ID's are hyperlinks that, when clicked, call QueryChem which displays the information from the corporate database for the compound identified by the specific ID number.

The tables are color-coded based on values defined in APTCO and the plotter utility. Green indicates compounds that showed inhibition based on the user defined threshold value. Red indicates an invalid point, not used in calculation. Light Grey indicates C+ and a darker grey indicates a C− value.

Located at the bottom of the page is a legend describing the color codes and three buttons. The first button is 'Print', which prints the report. The second button is executed 'Return to Upload'. When clicked, 'Return to Upload' causes the current project to close and returns the user to BioSelect. The third button is executed 'Edit Comments'.

When 'Edit Comments' is clicked, a script called editComments is executed that allows a user to edit the comments stored in the database relating to the analysis session.

editComments 410

The editComments component 410 is a script called by both bkBioReport 416 and bkBioReport2 (described above). The component 410 retrieves comments from the database that were defined in BioSelect 310 or BioSelectBDI 306 and displays the comments in a text area for editing.

When a user clicks 'Reset' in this window, the comments are refreshed from the database. When a user clicks 'Update', the contents of the text are submitted to updateComments 418.

updateComments 418

The updateComments component in an embodiment of this invention receives the comments and any changes made in the display of editComments 420 and these changes are updated to the database and the previous report page (bkBioReport 416 or bkBioReport2 (not shown)) is refreshed. It may also display a momentary 'success' message upon updating and automatically closes itself.

Compound Selection Template

The Compound Selection Template (not shown) allows the user to select areas of the plate that are to be related to an individual compound. The user selects which label they want to relate first, then the user clicks and drags over any number and combination of wells on the plate. These will be highlighted in dark-blue for the current label. When the user selects the next compound label, if there is more than one compound on the plate, then the selected areas of other labels will fade to a light-blue to designate that they have been used.

Once all compounds have been designated on the plate, the user selects the wells to be used for the "controls" of the assay. Light-grey to designate the control-plus, usually the maximum, and dark-grey to designate the control-minus, usually the background. Once the controls have been defined, the user may define the remaining area, if any, as invalid. The invalid regions will be colored black to easily display which areas will not be used.

When all regions have been designated, the user selects 'Next' to continue to the Concentration Selection Template.

Concentration Selection Template

In an embodiment of this invention, the Concentration Selection Template component is similar to the Compound Selection component or techlet, but it maintains the previous techlet's settings of invalid areas and control point areas, leaving the unused areas as white or cleared. The user again selects the concentrion they wish to relate and then clicks and drags over any number and combination of wells on the plate. These will be high-lighted in dark-blue for the current concentration. When the user selects the next concentration, if there is more than one concentration on the plate, then the selected areas of the other concentrations will fade to light-blue to designate that they have been used.

When all white regions have been designated, the user selects 'Next' to continue to the Assay Analysis.

An embodiment of the present invention may be used to perform numerical analysis in a variety of situations. For example, embodiments of the present invention may be used to perform molecular discovery, pharmaceutical data analysis, chemical efficacy result studies, statistical analysis, and other scientific and mathematical functions.

As is known to one skilled in the art, an embodiment of the present invention includes administrative components and data structures. Because data analyzed within the user interface according to the present invention may be considered confidential and/or proprietary, and embodiment of the present invention will also include various security features. Also, since embodiments of the present invention may be used to analyze, manipulate, and visualize various types of data, billing and licensing of the software may take many forms. For example, a developer of software according to the present invention may create each of the various components as a stand alone product for licensing purposes. Another developer may create a single integrated application that includes all of the above-described components.

The foregoing description of embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the present invention.

That which is claimed:

1. A data management system for managing data relating to a plurality of analyses, the system comprising:
   a processor configured to:
      receive at least one data point for a first analysis;
      receive at least one data point for a second analysis;
      receive a first derived data point extracted from the at least one data point for the first analysis;
      receive a second derived data point extracted from the at least one data point for the second analysis;
      generate a graphical data display including each data point and each derived data point; and
   a user interface configured to:
      receive an indication that one of the at least one data points for the first analysis and the at least one data points for the second analysis are to be excluded from the first derived data and the second derived data without changing the value of either the at least one data point for a first analysis or the at least one data point for the second analysis, and
      cause the graphical data display to be dynamically updated in response to the indication.

2. The data management system of claim 1 wherein the system comprises a plurality of computers, wherein each of the plurality of computers utilizes an operating system comprising one of UNIX, LINUX, WindowsOS, MacOS, or Solaris.

3. The data manaaement system of claim 2 wherein one of the plurality of computers utilizes a LINUX operating system and a second of the plurality of computers utilizes a Windows operating system and a third of the plurality of computers utilizes a Solaris operating system.

4. The data management system of claim 3 wherein the processor and user interface are distributed among at least the first, second and third computers.

5. The data management system of claim 1 wherein the indication that one of the at least one data point for the first analysis and the at least one data point for the second analysis are to be excluded from the first derived data and the second derived data, is based at least in part on the relative value of the at least one data point to be excluded in comparison to a threshold level.

6. The data management system of the claim 5 wherein the threshold level is variable.

7. The data management system of claim 1 wherein the indication that one of the at least one data point for the first analysis and the at least one data point for the second analysis are to be excluded from the first derived data and the second derived data, is based at least in part on a data fit analysis.

8. The data management system of claim 1 further comprising additional data points based on additional analyses and additional derived data points based on the additional data points.

9. The data management system of claim 8 wherein each analysis in the plurality of analyses comprises a data point corresponding to at least two or more of a composition's structure; a composition's biological activity; a composition's analytical data; a composition's identification number; or a composition's physical location.

10. The data management system of claim 1 wherein the display comprises a visual indication of an excluded data point.

11. The data management system of claim 1 wherein the system meets internet standards.

12. The data management system of claim 1 wherein the interface and display comprise a graphical user interface.

13. The data management system of claim 1 wherein the interface and display comprise a tool command line.

14. The data management system of claim 1 further comprising a first calculated data point calculated from the first derived data point and a second calculated data point calculated from the second derived data point wherein the excluded data point comprises a derived data point.

15. The data management system of claim 14 wherein the display comprises: first tabular data, second tabular data, first graphical data and second graphical data corresponding to first and second calculated data points.

* * * * *

UNITED STATES PATENT AND TRADEMARK OFFICE
CERTIFICATE OF CORRECTION

PATENT NO.       : 7,146,384 B2
APPLICATION NO.  : 10/411568
DATED            : December 5, 2006
INVENTOR(S)      : Reyad I. Sawafta It is certified that error appears in the above-identified patent and that said Letters Patent is hereby corrected as shown below:

Under "Cross Reference to Related Applications"

Column 1 Line 26, the phrase "No. 10/410,965entitled" should read --No. 10/410,965 entitled--

Column 5 Line 18 the word "tp" should read --to--

Column 6 Line 43 the word "a" should read --an--

Column 7 Line 27 the "plot1" should read --plot--

Column 7 Line 28 the word "features1" should read --features--

Column 7 Line 28 there should be a comma inserted between the words "features" and "can"--features, can also--

Column 7 Line 34 the word "lotter" should read --plotter--

Column 7 Line 55 the word "it's" should read --its--

Column 8 Line 4 the word "includes" should read --include--

Column 9, Line 3 the word "includes" should road --include--

Column 9 Line 17 the word "my" should read --may--

Colum 10 Line 62 the phrase "the named labels for" should be deleted.

Column 11 Line 43 the word "Stadard" should read --Standard--

Column 11 Line 63 the word "thp" should read --the--

Column 15, Line 67 the phrase "updateBDI info 506" should read --updateBDI_info 506--

Column 16 Line 63 the word "are" should read --is--

Column 20 Line 1 the word "data manaaement should read --data management--

UNITED STATES PATENT AND TRADEMARK OFFICE
CERTIFICATE OF CORRECTION

PATENT NO.         : 7,146,384 B2
APPLICATION NO.    : 10/411568
DATED              : December 5, 2006
INVENTOR(S)        : Reyad I. Sawafta It is certified that error appears in the above-identified patent and that said Letters Patent is hereby corrected as shown below:

Column 20 Line 13 the phrase "derived data, is based on" should read --derived data is based on--

Signed and Sealed this

Sixth Day of March, 2007

JON W. DUDAS
*Director of the United States Patent and Trademark Office*